United States Patent
McDonald et al.

(10) Patent No.: US 8,612,023 B2
(45) Date of Patent: Dec. 17, 2013

(54) SYSTEMS AND METHODS OF MAKING AND USING SUPPORT ELEMENTS FOR ELONGATED MEMBERS OF IMPLANTABLE ELECTRIC STIMULATION SYSTEMS

(71) Applicant: Boston Scientific Neuromodulation Corporation, Valencia, CA (US)

(72) Inventors: Matthew Lee McDonald, Pasadena, CA (US); Anne Margaret Pianca, Santa Monica, CA (US); Joshua Dale Howard, North Hollywood, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

(21) Appl. No.: 13/718,994

(22) Filed: Dec. 18, 2012

(65) Prior Publication Data
US 2013/0110186 A1    May 2, 2013

Related U.S. Application Data

(63) Continuation of application No. 12/499,626, filed on Jul. 8, 2009, now Pat. No. 8,340,782.

(51) Int. Cl.
*A61N 1/05*      (2006.01)
(52) U.S. Cl.
USPC ............................ 607/116; 607/117; 607/125
(58) Field of Classification Search
USPC ........... 607/46, 116, 117, 119, 122, 123, 125; 600/372, 373, 374, 377, 378
See application file for complete search history.

(56) References Cited

U.S. PATENT DOCUMENTS

| | | |
|---|---|---|
| 4,425,919 A | 1/1984 | Alston, Jr. et al. |
| 4,744,370 A | 5/1988 | Harris |
| 5,246,014 A | 9/1993 | Williams et al. |

(Continued)

FOREIGN PATENT DOCUMENTS

| | | |
|---|---|---|
| EP | 0618822 B1 | 1/1997 |
| EP | 0898483 B1 | 10/2003 |

(Continued)

OTHER PUBLICATIONS

U.S. Appl. No. 12/499,626, Official Communication mailed May 16, 2011.

(Continued)

*Primary Examiner* — Carl H Layno
*Assistant Examiner* — Eugene Wu
(74) *Attorney, Agent, or Firm* — Frommer Lawrence & Haug LLP; Patrick R. Turner

(57) ABSTRACT

An implantable lead includes a lead body. A plurality of conductors are disposed within the lead body and electrically couple at least one electrode to at least one terminal. At least one of the conductors includes a plurality of units. Each of the units includes a first conductor segment extending along the lead body from a beginning point to a first position, a second conductor segment extending from the first position to a second position, and a third conductor segment extending along the elongated member from the second position to an endpoint. The conductor segments are arranged so as to form alternating single-coil regions and multi-coil regions. At least one support element is disposed along at least a portion of at least one of the single-coil regions and is configured and arranged to increase the stiffness of the at least one of the single-coil regions.

20 Claims, 8 Drawing Sheets

(56) References Cited

U.S. PATENT DOCUMENTS

| | | |
|---|---|---|
| 5,308,342 A | 5/1994 | Sepetka et al. |
| 5,683,445 A | 11/1997 | Swoyer |
| 5,695,483 A | 12/1997 | Samson |
| 5,716,391 A | 2/1998 | Grandjean |
| 5,800,497 A | 9/1998 | Bakels et al. |
| 6,181,969 B1 | 1/2001 | Gord |
| 6,508,804 B2 | 1/2003 | Sarge et al. |
| 6,516,227 B1 | 2/2003 | Meadows et al. |
| 6,609,029 B1 | 8/2003 | Mann et al. |
| 6,609,032 B1 | 8/2003 | Woods et al. |
| 6,728,579 B1 | 4/2004 | Lindgren et al. |
| 6,741,892 B1 | 5/2004 | Meadows et al. |
| 7,239,923 B1 | 7/2007 | Tockman et al. |
| 7,244,150 B1 | 7/2007 | Brase et al. |
| 7,437,193 B2 | 10/2008 | Parramon et al. |
| 7,519,432 B2 | 4/2009 | Bolea et al. |
| 7,546,165 B2 | 6/2009 | Zarembo et al. |
| 7,672,734 B2 | 3/2010 | Anderson et al. |
| 7,761,165 B1 | 7/2010 | He et al. |
| 7,815,627 B2 | 10/2010 | Von Oepen et al. |
| 7,949,395 B2 | 5/2011 | Kuzma |
| 7,974,706 B2 | 7/2011 | Moffitt et al. |
| 8,175,710 B2 | 5/2012 | He |
| 8,224,450 B2 | 7/2012 | Brase |
| 8,340,782 B2 * | 12/2012 | McDonald et al. ........... 607/116 |
| 2003/0114905 A1 | 6/2003 | Kuzma |
| 2004/0059392 A1 | 3/2004 | Parramon et al. |
| 2004/0162601 A1 | 8/2004 | Smits |
| 2005/0165465 A1 | 7/2005 | Pianca et al. |
| 2006/0089691 A1 | 4/2006 | Kaplan et al. |
| 2006/0089692 A1 | 4/2006 | Cross et al. |
| 2006/0089695 A1 | 4/2006 | Bolea et al. |
| 2006/0089696 A1 | 4/2006 | Olsen et al. |
| 2006/0089697 A1 | 4/2006 | Cross et al. |
| 2006/0265038 A1 | 11/2006 | Hagen et al. |
| 2007/0142890 A1 | 6/2007 | Zarembo et al. |
| 2007/0150007 A1 | 6/2007 | Anderson et al. |
| 2007/0150036 A1 | 6/2007 | Anderson |
| 2007/0161294 A1 | 7/2007 | Brase et al. |
| 2007/0219595 A1 | 9/2007 | He |
| 2007/0239243 A1 | 10/2007 | Moffitt et al. |
| 2007/0239249 A1 | 10/2007 | Tockman et al. |
| 2008/0071320 A1 | 3/2008 | Brase |
| 2008/0119917 A1 | 5/2008 | Geistert |
| 2008/0262584 A1 | 10/2008 | Bottomley et al. |
| 2009/0222073 A1 | 9/2009 | Flowers et al. |
| 2009/0222074 A1 | 9/2009 | Zarembo et al. |
| 2010/0114277 A1 | 5/2010 | Zhao et al. |
| 2011/0009932 A1 | 1/2011 | McDonald et al. |
| 2011/0093053 A1 | 4/2011 | Djurling et al. |

FOREIGN PATENT DOCUMENTS

| | | |
|---|---|---|
| EP | 0939658 B1 | 10/2003 |
| EP | 1171193 B1 | 11/2004 |
| WO | WO-9308817 A1 | 5/1993 |
| WO | WO-9707851 A1 | 3/1997 |
| WO | WO-9740883 A1 | 11/1997 |
| WO | WO-0056396 A1 | 9/2000 |
| WO | WO-2006047145 A1 | 5/2006 |
| WO | WO-2006047168 A1 | 5/2006 |
| WO | WO-2006047177 A1 | 5/2006 |
| WO | WO-2006047178 A1 | 5/2006 |
| WO | WO-2006047179 A1 | 5/2006 |
| WO | WO-2007078360 A2 | 7/2007 |

OTHER PUBLICATIONS

U.S. Appl. No. 12/499,626, Official Communication mailed Oct. 19, 2011.

U.S. Appl. No. 12/499,626, Official Communication mailed Mar. 19, 2012.

* cited by examiner

SYSTEMS AND METHODS OF MAKING AND USING SUPPORT ELEMENTS FOR ELONGATED MEMBERS OF IMPLANTABLE ELECTRIC STIMULATION SYSTEMS

CROSS-REFERENCE TO RELATED APPLICATIONS

This patent application is a continuation of U.S. patent application Ser. No. 12/499,626 filed on Jul. 8, 2009 now U.S. Pat. No. 8,340,782, which is incorporated herein by reference.

FIELD

The present invention is directed to the area of implantable electrical stimulation systems and methods of making and using the systems. The present invention is also directed to implantable electrical stimulation leads having elongated members with one or more support elements disposed along portions of the elongated members, as well as methods of making and using the support elements, elongated members, and electrical stimulation systems.

BACKGROUND

Implantable electrical stimulation systems have proven therapeutic in a variety of diseases and disorders. For example, spinal cord stimulation systems have been used as a therapeutic modality for the treatment of chronic pain syndromes. Peripheral nerve stimulation has been used to treat chronic pain syndrome and incontinence, with a number of other applications under investigation. Functional electrical stimulation systems have been applied to restore some functionality to paralyzed extremities in spinal cord injury patients.

Stimulators have been developed to provide therapy for a variety of treatments. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue.

Conventional implanted electrical stimulation systems are often incompatible with magnetic resonance imaging ("MRI") due to the large radio frequency ("RF") pulses used during MRI. The RF pulses can generate transient signals in the conductors and electrodes of an implanted lead. These signals can have deleterious effects including, for example, unwanted heating of the tissue causing tissue damage, induced currents in the lead, or premature failure of electronic components.

BRIEF SUMMARY

In one embodiment, an implantable lead includes a lead body. A plurality of electrodes are disposed on a distal end of the lead body. A plurality of terminals are disposed on a proximal end of the lead body. A plurality of conductors are disposed within an outer layer of the lead body. Each conductor electrically couples at least one of the electrodes to at least one of the terminals. At least one of the conductors includes a plurality of units. Each of the units includes a first conductor segment extending along the lead body from a beginning point to a first position, a second conductor segment extending from the first position to a second position, and a third conductor segment extending along the elongated member from the second position to an endpoint. The conductor segments are arranged so as to form alternating single-coil regions and multi-coil regions. The implantable lead also includes at least one support element disposed along at least a portion of at least one of the single-coil regions. The at least one support element is configured and arranged to increase the stiffness of the at least one of the single-coil regions.

In another embodiment, an electrical stimulating system includes a lead. a plurality of electrodes are disposed on a distal end of the lead. A plurality of terminals are disposed on a proximal end of the lead. A plurality of conductors are disposed within an outer layer of the lead. Each conductor electrically couples at least one of the electrodes to at least one of the terminals. At least one of the conductors includes a plurality of units. Each of the units includes a first conductor segment extending along the lead body from a beginning point to a first position, a second conductor segment extending from the first position to a second position, and a third conductor segment extending along the elongated member from the second position to an endpoint. The conductor segments are arranged so as to form alternating single-coil regions and multi-coil regions. The implantable lead also includes at least one support element disposed along at least a portion of at least one of the single-coil regions. The at least one support element is configured and arranged to increase the stiffness of the at least one of the single-coil regions. The electrical stimulating system also includes a control module and a connector. The control module is configured and arranged to electrically couple to the proximal end of the lead. The control module includes a housing and an electronic subassembly disposed in the housing. The connector is configured and arranged to receive the lead. The connector has a proximal end, a distal end, and a longitudinal length. The connector includes a connector housing and a plurality of connector contacts disposed in the connector housing. The connector housing defines a port at the distal end of the connector. The port is configured and arranged for receiving the proximal end of the lead. The a plurality of connector contacts are disposed in the connector housing and are configured and arranged to couple to at least one of the plurality of terminals disposed on the proximal end of the lead.

In yet another embodiment, a method for forming an implantable lead includes forming an elongated conductor into a plurality of units that include a first conductor segment extending in a first direction from a beginning point to a first position, a second conductor segment extending in a second direction that is opposite to the first direction from the first position to a second position, and a third conductor segment extending in the first direction from the second position to an endpoint, wherein the conductor segments are arranged so as to form alternating single-coil regions and multi-coil regions along a length of the conductor. A support element is disposed along at least a portion of at least one of the single-coil regions to increase the stiffness of each of the at least one single-coil region. The conductor is disposed in an elongated outer layer. A first end of the conductor is coupled to an electrode. A second end of the conductor is coupled to a terminal.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention is directed to the area of implantable electrical stimulation systems and methods of making and using the systems. The present invention is also directed to implantable electrical stimulation leads having elongated members with one or more support elements disposed along portions of the elongated members, as well as methods of making and using the support elements, elongated members, and electrical stimulation systems.

Suitable implantable electrical stimulation systems include, but are not limited to, an electrode lead ("lead") with one or more electrodes disposed on a distal end of the lead and one or more terminals disposed on one or more proximal ends of the lead. Leads include, for example, percutaneous leads, paddle leads, and cuff leads. Examples of electrical stimulation systems with leads are found in, for example, U.S. Pat. Nos. 6,181,969; 6,516,227; 6,609,029; 6,609,032; 6,741,892; 7,244,150; 7,672,734; 7,761,165; 7,949,395; 7,974,706; and 8,175,710; and U.S. Patent Application Publications Nos. 2005/0165465 and 2007/0150036, all of which are incorporated by reference.

Figure 1:
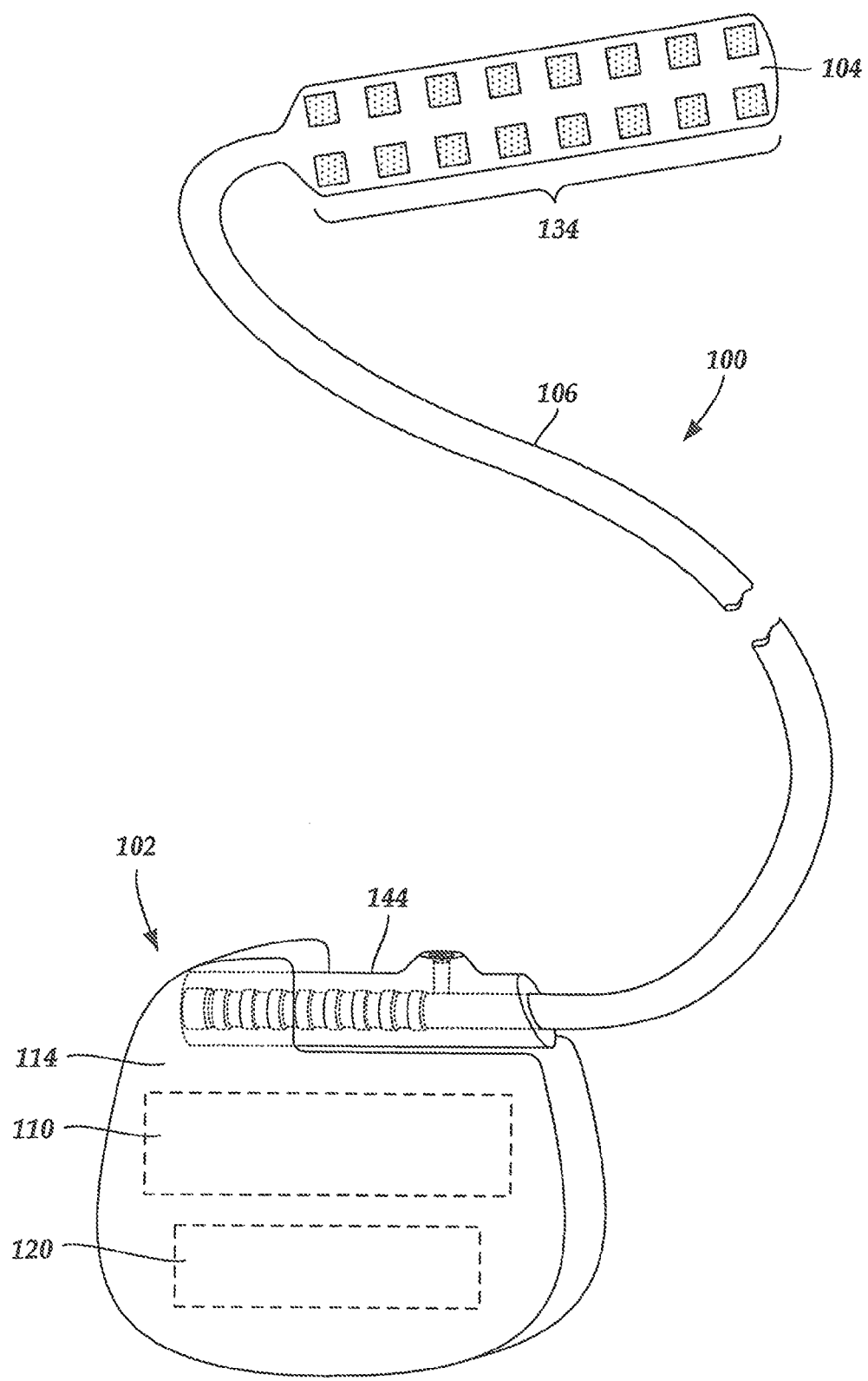
FIG. 1 is a schematic view of one embodiment of an electrical stimulation system, according to the invention.
Figure 2:
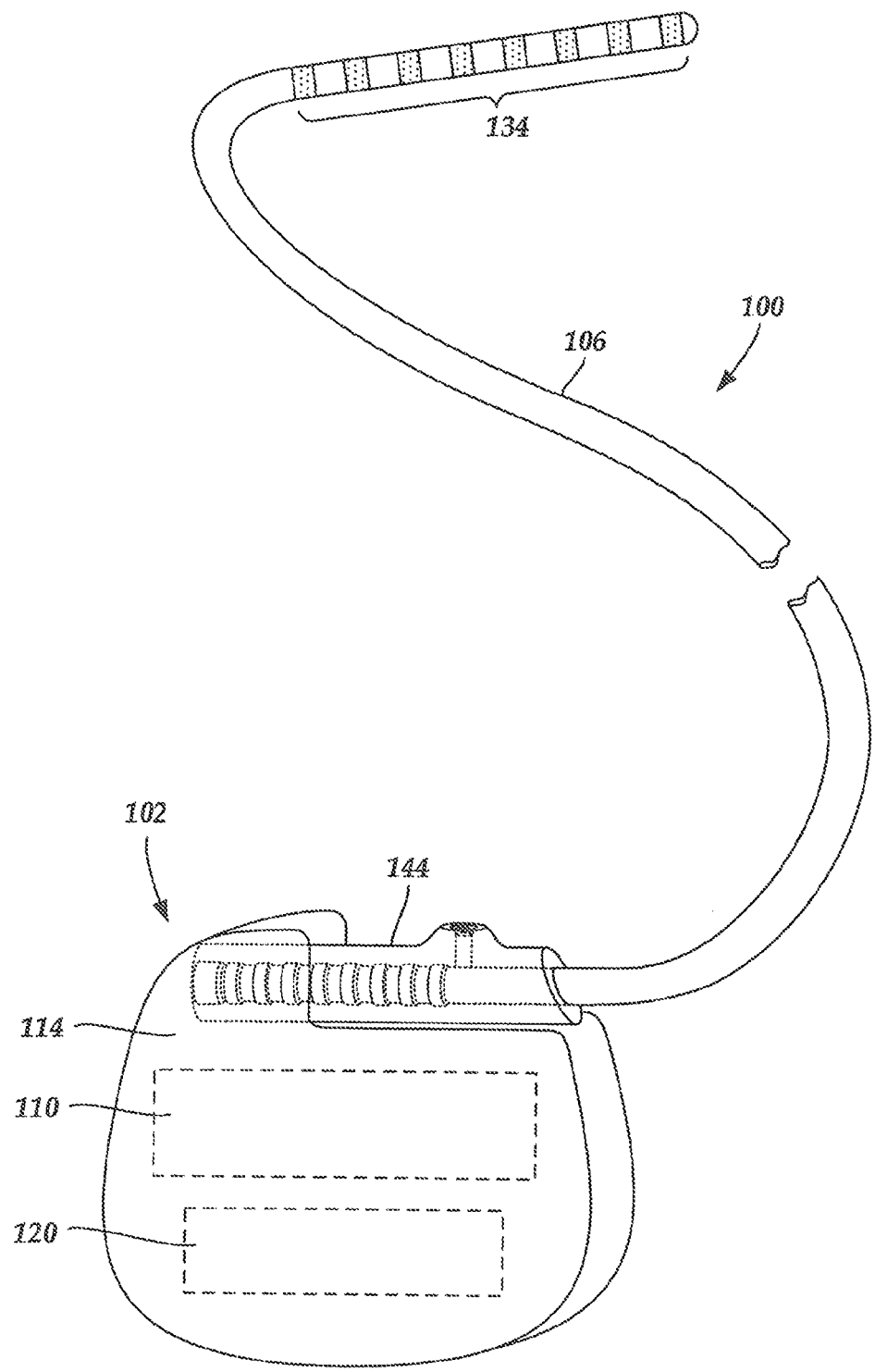
FIG. 2 is a schematic view of another embodiment of an electrical stimulation system, according to the invention.

FIG. 1 illustrates schematically one embodiment of an electrical stimulation system 100. The electrical stimulation system includes a control module (e.g., a stimulator or pulse generator) 102, a paddle body 104, and at least one lead body 106 coupling the control module 102 to the paddle body 104. The paddle body 104 and the one or more lead bodies 106 form a lead. The paddle body 104 typically includes an array of electrodes 134. The control module 102 typically includes an electronic subassembly 110 and an optional power source 120 disposed in a sealed housing 114. The control module 102 typically includes a connector 144 (FIGS. 2 and 3A, see also 322 and 350 of FIG. 3B) into which the proximal end of the one or more lead bodies 106 can be plugged to make an electrical connection via conductive contacts on the control module 102 and terminals (e.g., 310 in FIG. 3A and 336 of FIG. 3B) on each of the one or more lead bodies 106. It will be understood that the electrical stimulation system can include more, fewer, or different components and can have a variety of different configurations including those configurations disclosed in the electrical stimulation system references cited herein. For example, instead of a paddle body 104, the electrodes 134 can be disposed in an array at or near the distal end of the lead body 106 forming a percutaneous lead, as illustrated in FIG. 2. A percutaneous lead may be isodiametric along the length of the lead. In addition, one or more lead extensions 312 (see FIG. 3B) can be disposed between the one or more lead bodies 106 and the control module 102 to extend the distance between the one or more lead bodies 106 and the control module 102 of the embodiments shown in FIGS. 1 and 2.

The electrical stimulation system or components of the electrical stimulation system, including one or more of the lead bodies 106, the paddle body 104, and the control module 102, are typically implanted into the body of a patient. The electrical stimulation system can be used for a variety of applications including, but not limited to, brain stimulation, neural stimulation, spinal cord stimulation, muscle stimulation, and the like.

The electrodes 134 can be formed using any conductive, biocompatible material. Examples of suitable materials include metals, alloys, conductive polymers, conductive carbon, and the like, as well as combinations thereof. The number of electrodes 134 in the array of electrodes 134 may vary. For example, there can be two, four, six, eight, ten, twelve, fourteen, sixteen, or more electrodes 134. As will be recognized, other numbers of electrodes 134 may also be used.

The electrodes of the paddle body 104 or one or more lead bodies 106 are typically disposed in, or separated by, a non-conductive, biocompatible material including, for example, silicone, polyurethane, polyetheretherketone ("PEEK"), epoxy, and the like or combinations thereof. The paddle body 104 and one or more lead bodies 106 may be formed in the desired shape by any process including, for example, molding (including injection molding), casting, and the like. Electrodes and connecting wires can be disposed onto or within a paddle body either prior to or subsequent to a molding or casting process. The non-conductive material typically extends from the distal end of the lead to the proximal end of each of the one or more lead bodies 106. The non-conductive, biocompatible material of the paddle body 104 and the one or more lead bodies 106 may be the same or different. The paddle body 104 and the one or more lead bodies 106 may be a unitary structure or can be formed as two separate structures that are permanently or detachably coupled together.

Terminals (e.g., 310 in FIG. 3A and 336 of FIG. 3B) are typically disposed at the proximal end of the one or more lead bodies 106 for connection to corresponding conductive contacts (e.g., 314 in FIG. 3A and 340 of FIG. 3B) in connectors (e.g., 144 in FIGS. 1-3A and 322 and 350 of FIG. 3B) disposed on, for example, the control module 102 (or to other devices, such as conductive contacts on a lead extension, an operating room cable, or an adaptor). Conductive wires ("conductors") (not shown) extend from the terminals (e.g., 310 in FIG. 3A and 336 of FIG. 3B) to the electrodes 134. Typically, one or more electrodes 134 are electrically coupled to a terminal (e.g., 310 in FIG. 3A and 336 of FIG. 3B). In some embodiments, each terminal (e.g., 310 in FIG. 3A and 336 of FIG. 3B) is only connected to one electrode 134. The conductive wires may be embedded in the non-conductive material of the lead or can be disposed in one or more lumens (not shown) extending along the lead. In some embodiments, there is an individual lumen for each conductive wire. In other embodiments, two or more conductive wires may extend through a lumen. There may also be one or more lumens (not shown) that open at, or near, the proximal end of the lead, for example, for inserting a stylet rod to facilitate placement of the lead within a body of a patient. Additionally, there may also be one or more lumens (not shown) that open at, or near, the distal end of the lead, for example, for infusion of drugs or medication into the site of implantation of the paddle body 104. In at least one embodiment, the one or more lumens may be flushed continually, or on a regular basis, with saline, epidural fluid, or the like. In at least some embodiments, the one or more lumens can be permanently or removably sealable at the distal end.

Figure 3A:
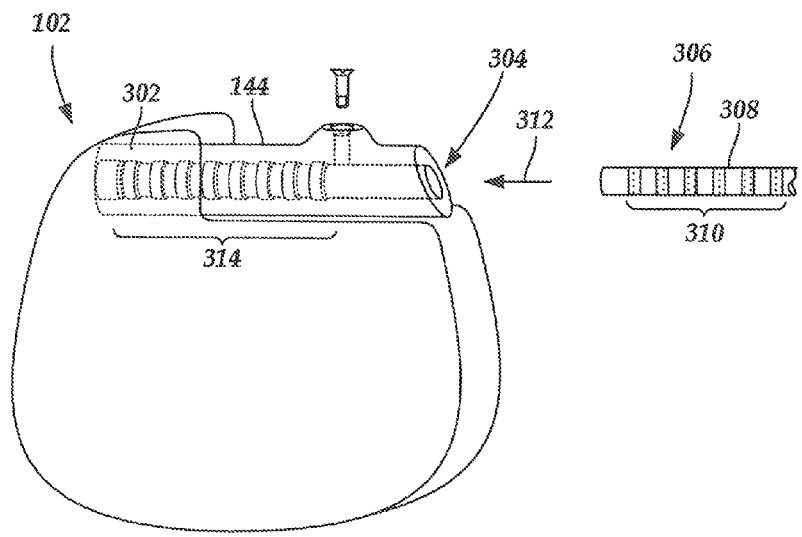
FIG. 3A is a schematic view of one embodiment of a proximal portion of a lead and a control module of an electrical stimulation system, according to the invention.

In at least some embodiments, leads are coupled to connectors disposed on control modules. In FIG. 3A, a lead 308 is shown configured and arranged for insertion to the control module 102. The connector 144 includes a connector housing 302. The connector housing 302 defines at least one port 304 into which a proximal end 306 of a lead 308 with terminals 310 can be inserted, as shown by directional arrow 312. The connector housing 302 also includes a plurality of conductive contacts 314 for each port 304. When the lead 308 is inserted into the port 304, the conductive contacts 314 can be aligned with the terminals 310 on the lead 308 to electrically couple the control module 102 to the electrodes (134 of FIG. 1) disposed at a distal end of the lead 308. Examples of connectors in control modules are found in, for example, U.S. Pat. Nos. 7,244,150 and 8,224,450, which are incorporated by reference.

Figure 3B:
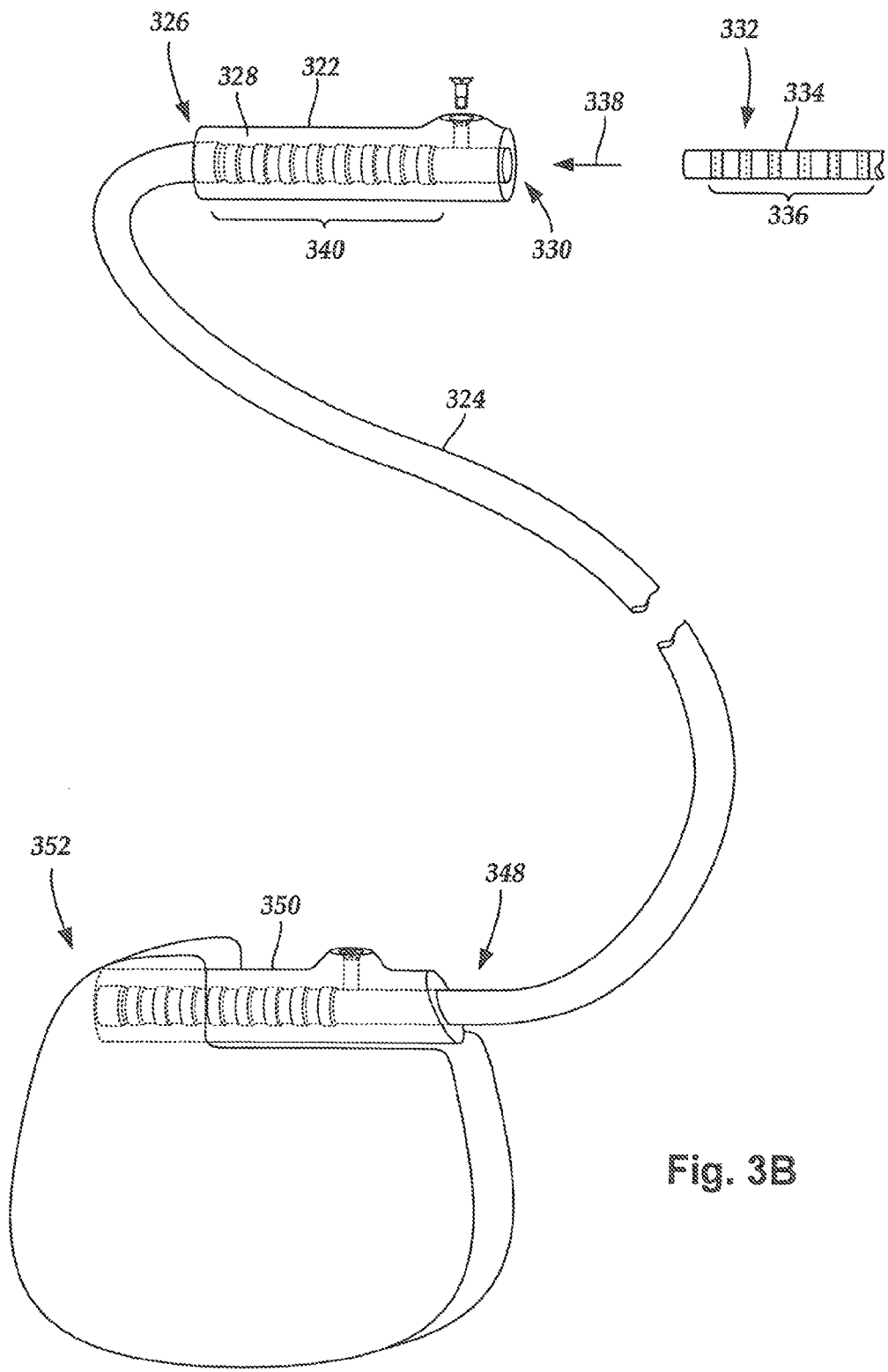
FIG. 3B is a schematic view of one embodiment of a proximal portion of a lead and a lead extension of an electrical stimulation system, according to the invention.

In FIG. 3B, a connector 322 is disposed on a lead extension 324. The connector 322 is shown disposed at a distal end 326 of the lead extension 324. The connector 322 includes a connector housing 328. The connector housing 328 defines at least one port 330 into which a proximal end 332 of a lead 334 with terminals 336 can be inserted, as shown by directional arrow 338. The connector housing 328 also includes a plurality of conductive contacts 340. When the lead 334 is inserted into the port 330, the conductive contacts 340 disposed in the connector housing 328 can be aligned with the terminals 336 on the lead 334 to electrically couple the lead extension 324 to the electrodes (134 of FIG. 1) disposed at a distal end (not shown) of the lead 334.

In at least some embodiments, the proximal end of a lead extension is similarly configured and arranged as a proximal end of a lead. The lead extension 324 may include a plurality of conductive wires (not shown) that electrically couple the conductive contacts 340 to a proximal end 348 of the lead extension 324 that is opposite to the distal end 326. In at least some embodiments, the conductive wires disposed in the lead extension 324 can be electrically coupled to a plurality of terminals (not shown) disposed on the proximal end 348 of the lead extension 324. In at least some embodiments, the proximal end 348 of the lead extension 324 is configured and arranged for insertion into a connector disposed in another lead extension. In other embodiments, the proximal end 348 of the lead extension 324 is configured and arranged for insertion into a connector disposed in a control module. As an example, in FIG. 3B the proximal end 348 of the lead extension 324 is inserted into a connector 350 disposed in a control module 352.

One or more of the conductors connecting at least one terminal to an electrode (or other conductive contact) can be arranged in a conductor path to eliminate or reduce the effect of RF irradiation, such as that generated during magnetic resonance imaging ("MRI"). The conductor path includes a plurality of units arranged in series. In some embodiments, the units are disposed along a single continuous conductor. In other embodiments, the units are separate conductive elements electrically coupled together.

Each unit includes at least three conductor segments that at least partially overlap one another to form a multi-coil region. First, each unit includes a first conductor segment that extends in a first direction along a longitudinal length of an elongated member (e.g., a lead or lead extension) from a beginning point to a first position. Second, each unit includes a second conductor segment that extends from the first position back towards (and possibly past) the beginning point to a second position. Third, each unit includes a third conductor segment that extends in the first direction from the second position to an endpoint. In at least some embodiments, the first position is between the second position and the endpoint. In at least some embodiments, the second position is between the beginning point and the first position. In at least some embodiments, the unit may include a single-coil region flanking at least one end of the multi-coil region.

The units may be electrically continuous such that the endpoint of a first unit is the beginning point of the next consecutive unit. At least one of the beginning points may be a terminal or an electrode (or other conductive contact). Likewise, at least one of the endpoints may be a terminal or an electrode (or other conductive contact). In preferred embodiments, the conductor segments are each coiled. In at least some embodiments, the conductor segments are coiled around a conductor placement sleeve. In at least some embodiments, the conductor placement sleeve defines a lumen that optionally is configured and arranged to receive a stiffening member (e.g., a stylet, or the like).

In at least some embodiments, at least one of the first, second, or third conductor segments is substantially straight. In at least some embodiments, the first and third conductor segments are substantially straight and the second conductor segment is coiled. In at least some other embodiments, all three conductor segments are substantially straight. It will be understood that the term "substantially straight conductor segment" means that the conductor segment is not coiled. A "substantially straight conductor segment" may be curved, particularly when the lead itself is curved (see, for example, FIG. 1).

In at least some embodiments, the conductor segments are all formed from the same length of conductive material (e.g., wire or the like). The conductors may have a single filament or be multi-filar. In preferred embodiments, the conductors are multi-filar. In at least some embodiments, two or more of the conductor segments can be individual pieces of conductive material that are electrically coupled (e.g., soldered or welded) together. In at least some embodiments, a layer of insulation ("conductor insulation") is disposed over each of the conductor segments.

In at least some embodiments, the length of conductor used in the second conductor segment is at least 1.5, 1.75, 1.9, 2, 2.1, 2.25, or 2.5 times the length of either the first conductor segment or the third conductor segment. It will be recognized, however, that this ratio of conductor-segment lengths may vary among embodiments, particularly if the thickness of the conductor or thickness of the layer of conductor insulation is different for the different segments.

Figure 4:
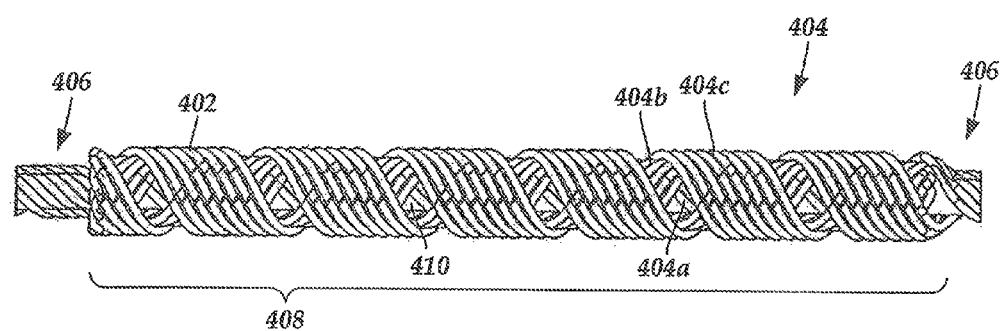
FIG. 4 is a schematic side view of one embodiment of portions of a plurality of conductors disposed along a conductor placement sleeve, the conductors configured into units, according to the invention.

FIG. 4 schematically illustrates one embodiment of a plurality of conductors 402. The conductors 402 are configured into a plurality of units, such as unit 404. Each unit includes a first conductor segment 404a, a second conductor segment 404b, and a third conductor segment 404c. In at least some embodiments, conductor insulation is disposed over the conductors 402 to electrically isolate each of the conductors 402 from one another.

Many different numbers of units may be disposed along longitudinal lengths of the conductors 402 including, for example, two, three, four, five, six, seven, eight, nine, ten, twelve, fifteen, twenty, twenty-five, thirty, forty, fifty, or more units. It will be understood that many other numbers of units may be employed as well. When a plurality of units are coupled together in series along a longitudinal length of one or more conductors, the plurality of units form a repeating series of single-coil regions, such as the single-coil regions 406, separated from one another by a multi-coil region, such as the multi-coil region 408.

In at least some embodiments, the conductors 402 are disposed along a conductor placement sleeve 410. The conductor placement sleeve 410 can be formed from any suitable biocompatible material including, for example, one or more polymers. In at least some embodiments, conductor insulation is disposed over the conductors 402 to encapsulate the conductors 402 and electrically isolate the conductors 402 from one another.

In at least some embodiments, one or more conductors having one or more units may be disposed in an elongated member (e.g., a lead or lead extension). In at least some embodiments, the ends of the conductors 402 can be coupled to terminals, electrodes, or conductive contacts. In preferred embodiments, each of the conductors in an elongated member are configured into units. In at least some embodiments, only a subset of the conductors disposed in an elongated member include one or more units, the remaining conductors having a different arrangement (for example, a single conductor segment between the terminal(s) and electrode(s)/conductive contact(s)).

Figure 5:
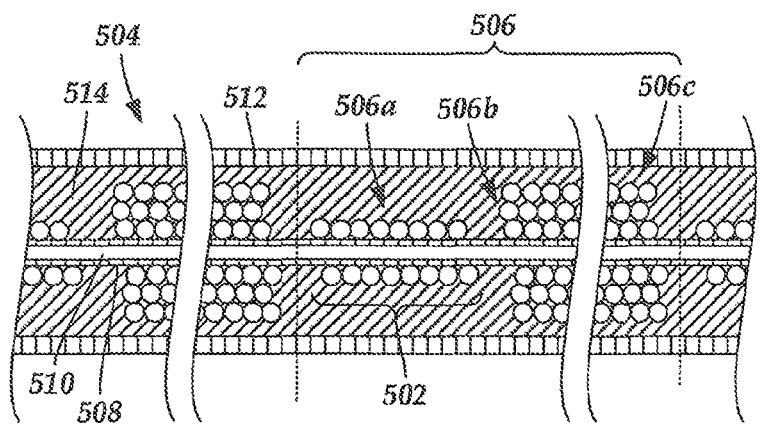
FIG. 5 is a schematic longitudinal cross-sectional view of one embodiment of portions of a plurality of conductors disposed in an elongated member, according to the invention.

Conductors, such as the conductors 402, may be disposed in a lumen of an elongated member (e.g., a lead, lead extension, or the like). FIG. 5 is a schematic longitudinal cross-sectional view of one embodiment of portions of a plurality of conductors 502 disposed in an elongated member 504. The illustrated portions of the conductors 502 includes unit 506, shown between two vertical dotted lines. Unit 506 includes a first conductor segment 506a, a second conductor segment 506b, and a third conductor segment 506c. In at least some embodiments, the conductors 502 are disposed over a conductor placement sleeve 508. In at least some embodiments, the conductor placement sleeve 508 defines a lumen 510. The elongated member 504 includes a body 512 and a lumen 514 into which the conductors 502 are disposed.

Figure 6A:
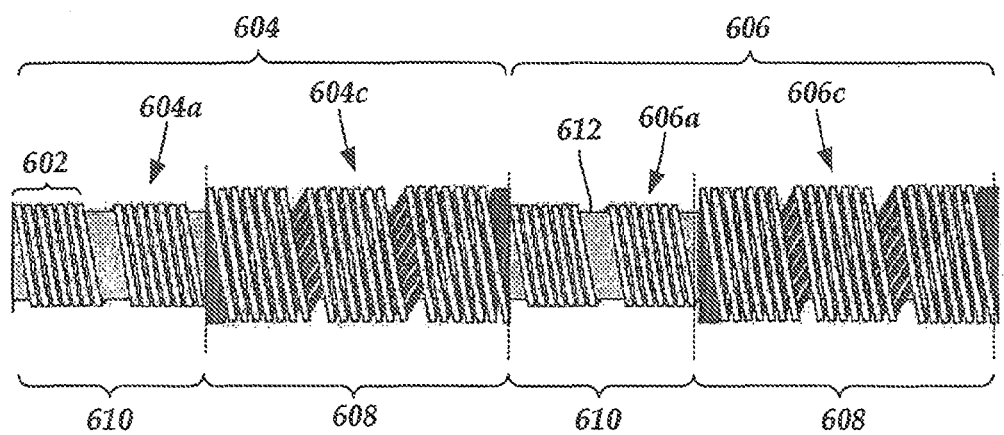
FIG. 6A is a schematic side view of one embodiment of a plurality of portions of conductors formed into two units that include alternating single-coil regions and multi-coil regions, according to the invention.

FIG. 6A schematically illustrates a side view of one embodiment of a plurality of conductors 602 each including units 604 and 606. In FIG. 6A, the first, second, and third conductor segments 604a, 604b (not shown in FIG. 6A), and 604c, respectively, of the unit 604, and the first, second, and third conductor segments 606a, 606b (not shown in FIG. 6A), and 606c, respectively, of the unit 606, are each coiled. The conductors 602 are arranged such that the conductors include multi-coil regions 608 and single-coil regions 610. In at least some embodiments, the conductors 602 may be coiled around one or more objects, such as a conductor placement sleeve 612.

Figure 6B:
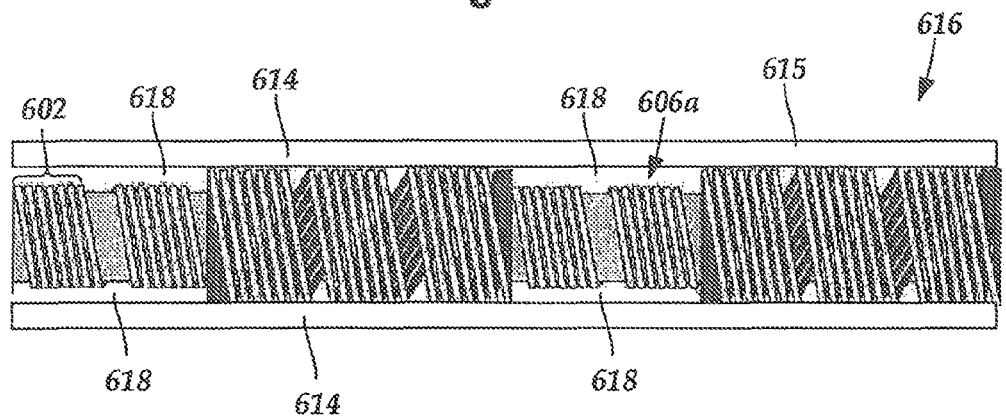
FIG. 6B is a schematic longitudinal cross-sectional view of one embodiment of the portions of conductors of FIG. 6A, according to the invention.

FIG. 6B is a schematic longitudinal cross-sectional view of the plurality of conductors 602 disposed in an outer layer 614 of a body 615 of a lead 616. When the outer layer 614 of the body 615 is isodiametric along the longitudinal length of the lead 616, open spaces 618 may form between the single-coil regions, such as single-coil region 606a, and the outer layer 614.

Multi-coil regions may be less susceptible than regions adjacent to the multi-coil regions (e.g., single-coil regions, regions adjacent to electrodes, regions adjacent to terminals, connectors, or the like) to premature failure during handling, implantation, or even during normal patient movement post-implantation. Thus, bending of the conductor may result in stress concentrations forming at single-coil regions and at end regions. Additionally, steering of the elongated member during implantation may be more difficult when the elongated member does not have a uniform strength (or stiffness) along the longitudinal length of the elongated member.

A support element is provided to increase the stiffness, as well as the strength, of the one or more portions of the conductors. In at least some embodiments, the support element is provided to increase the stiffness, as well as the strength, of regions adjacent to multi-coil regions (e.g., single-coil regions, regions adjacent to electrodes, regions adjacent to terminals, or the like). In at least some embodiments, the support element increases the stiffness of regions adjacent to multi-coil regions by at least 5%. In at least some embodiments, the support element increases the stiffness of regions adjacent to multi-coil regions by at least 10%. In at least some embodiments, the support element increases the stiffness of regions adjacent to multi-coil regions by at least 15%. In at least some embodiments, the support element increases the stiffness of regions adjacent to multi-coil regions by at least 20%. In at least some embodiments, the support element increases the stiffness of regions adjacent to multi-coil regions by at least 25%. In at least some embodiments, the support element increases the stiffness of regions adjacent to multi-coil regions by at least 30%. Strength (or stiffness) can be measured in various ways, for example, performing a three-point bending test where the force used to deflect a given region by a set amount is measured.

The support elements can be formed using any biocompatible material, including plastic (e.g., silicone rubber, polytetrafluoroethylene, PEEK, polyvinylidene fluoride, polyethylene terephthalate, urethane-silicone copolymers polyimide, polyamide, or the like or combinations thereof), metal, thermosets, thermoplastics, liquid crystal polymers, shape memory materials (polymer or metal based), hydrogels, porous plastics, combined metal products (such as metal-to-metal composite), or the like or combinations thereof.

Support elements can be formed from a radiopaque material. For example, support elements can be formed from a metal or a polymer doped with an agent, such as barium sulfate. Support elements may include materials that are, for example, braided, formed as a mesh, coiled, woven, and the like or combinations thereof. In at least some embodiments, at least a portion of the support elements are encased in a polymer prior to, or subsequent to, being applied to the conductors 602. In at least some embodiments, at least a portion of the support elements are encased in a polymer prior to, or subsequent to, being disposed in the outer layer 614 of the lead 616.

In FIGS. 7-12, the support elements (702, 802, 902, 1002, 1102, or 1202 in FIGS. 7-12, respectively) are described in relation to the lead 616. It will be understood that the support elements (702, 802, 902, 1002, 1102, or 1202 in FIGS. 7-12, respectively) may be employed in conjunction with a lead extension (e.g., the lead extension 324 of FIG. 3B) in addition to, or in lieu of, the lead 616. It will also be understood that different types of support elements may be used along a longitudinal length of the lead 616 to alter one or more characteristics along the longitudinal length of the lead 616 (e.g., strength, stiffness, or the like). Different types of support elements may be used along a longitudinal length of the lead 616 depending the region over which the support element is disposed. For example, a first type of support element may be disposed over a single-coil region and a second type of support element may be disposed over (or in proximity to) an electrode or terminal.

As shown in FIGS. 7-12, the support elements may be disposed in a number of different locations or arrangements. In some embodiments, the support elements are incorporated into the sleeve 612. In some embodiments, the support elements are disposed between the conductor placement sleeve 612 and the single-coil regions 610. In some embodiments, the support elements are disposed between the single-coil region 610 and the outer layer 614 of the lead 616. In some embodiments, the support elements are disposed over the outer layer 614 of the lead 616.

Figure 7:
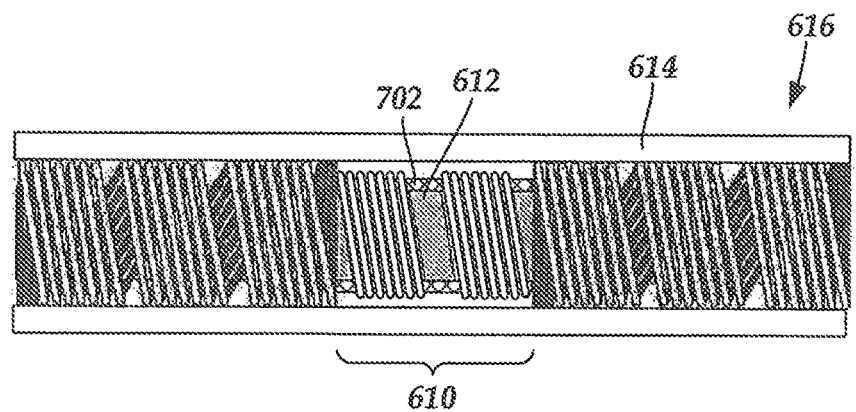
FIG. 7 is a schematic longitudinal cross-sectional view of one embodiment of a support element disposed under the single-coil region of FIG. 6B, according to the invention.

In some embodiments, the support element is disposed beneath the single-coil region. FIG. 7 is a schematic longitudinal cross-sectional view of one embodiment of the single-coil region 610 coiled around the conductor placement sleeve 612 and disposed in the outer layer 614 of the lead 616. A support element 702 is disposed within the conductor placement sleeve 612. It will be understood that the support element 702 may be disposed within all, or a portion, of the conductor placement sleeve 612.

In some embodiments, the support element 702 is implemented by forming the conductor placement sleeve 612 such that the conductor placement sleeve 612 includes reinforced regions onto which the single-coil regions of the conductors are disposed that have increased strength (or stiffness) from the regions onto which the multi-coil regions of the conductors are disposed. The regions of the conductor placement sleeve 612 with increased strength (or stiffness) may be implemented in many different ways including, for example, increasing the thickness of the conductor placement sleeve 612 along the regions of the conductor placement sleeve 612 onto which the single-coil regions of the conductors are disposed, forming the regions of the conductor placement sleeve 612 onto which the single-coil regions of the conductors are disposed of a stronger (or stiffer) material than the material used to form regions of the conductor placement sleeve 612 onto which the multi-coil regions of the conductors are disposed, or the like or combinations thereof.

In some embodiments, the support element 702 is disposed over the conductor placement sleeve 612. In at least some embodiments, the support element is disposed over the conductor placement sleeve and beneath the single-coil regions. In at least some embodiments, when the support element 702 is disposed over the conductor placement sleeve 612, the support element 702 is slid over the conductor placement sleeve 612 (e.g., a hypotube, heat shrink tubing, other tubing, a braided or mesh element, or the like). In at least some embodiments, when the support element 702 is disposed over the conductor placement sleeve 612, the support element 702 is wrapped or coiled over the conductor placement sleeve 612. It will be understood that the support element 702 may be disposed over all, or a portion, of the conductor placement sleeve 612.

Figure 8:
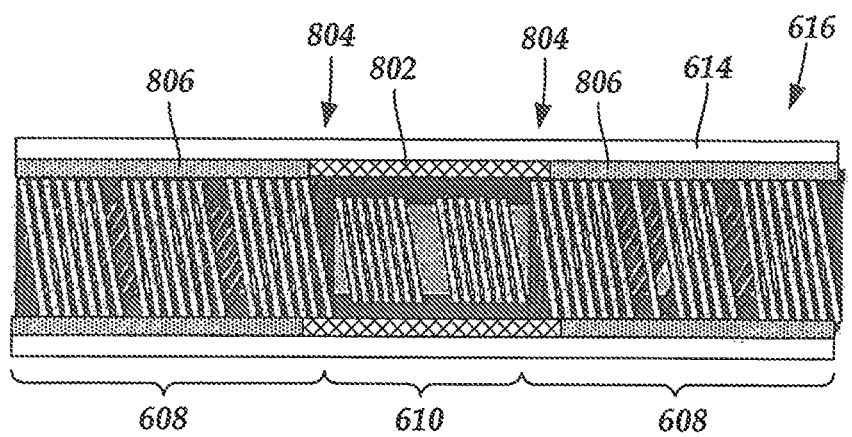
FIG. 8 is a schematic longitudinal cross-sectional view of a first embodiment of a support element disposed over the single-coil region of FIG. 6B, according to the invention.

In at least some embodiments, the support element is disposed over the single-coil region of the conductor and within the outer layer of the lead. FIG. 8 is a schematic longitudinal cross-sectional view of one embodiment of the single-coil region 610 disposed in the outer layer 614 of the lead 616. A support element 802 is disposed over the single-coil region 610. In at least some embodiments, the support element 802 spans a portion of the single-coil region 610. In at least some embodiments, the support element 802 spans the entire single-coil region 610.

In at least some embodiments, the ends 804 of the support element 802 are disposed on the flanking multiple-length regions 608 and the support element 802 spans a longitudinal length of the single-length region 610. In at least some embodiments, the support element 802 is formed from a material that is rigid enough to not bend radially inward under its own weight along the single-coil region 610. In at least some embodiments, one or more spacing elements 806 (e.g., tubing, wound strips of material, or the like) may be disposed over portions of the multi-coil regions 608 over which the support element 802 is not disposed in order for the lead 616 to be isodiametric.

Figure 9:
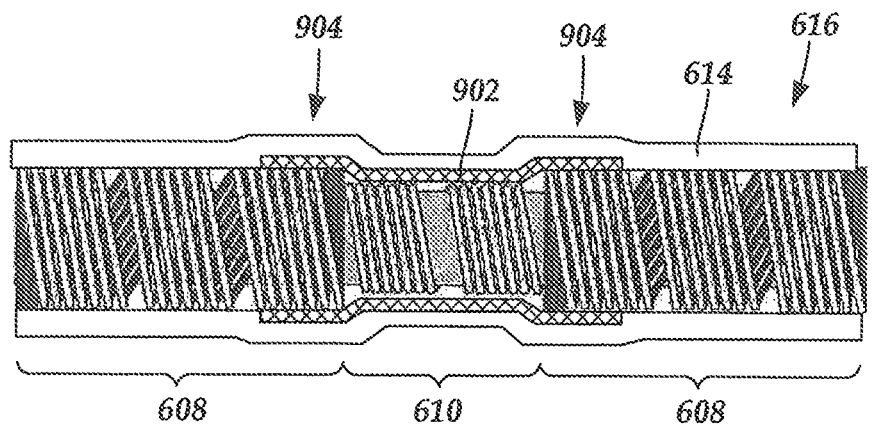
FIG. 9 is a schematic longitudinal cross-sectional view of a second embodiment of a support element disposed over the single-coil region of FIG. 6B, according to the invention.

In at least some embodiments, the support element is non-isodiametric, or results in a non-isodiametric lead. FIG. 9 is a schematic longitudinal cross-sectional view of one embodiment of the single-coil region 610 disposed in the outer layer 614 of the lead 616. A non-isodiametric support element 902 is disposed over the single-coil region 610. In at least some embodiments, the non-isodiametric support element 902 has ends 904 that are disposed on the flanking multiple-length regions 608 and the support element 902 spans the longitudinal length of the single-length region 610 such that a middle portion of the support element 902 bends or curves radially inward along at least a portion of the single-coil region 610. In at least some embodiments, one or more spacing elements (e.g., spacing elements 806 in FIG. 8) may be disposed over portions of the multi-coil regions 608 over which the support element 902 is not disposed in order for the lead 616 to be isodiametric.

Figure 10:
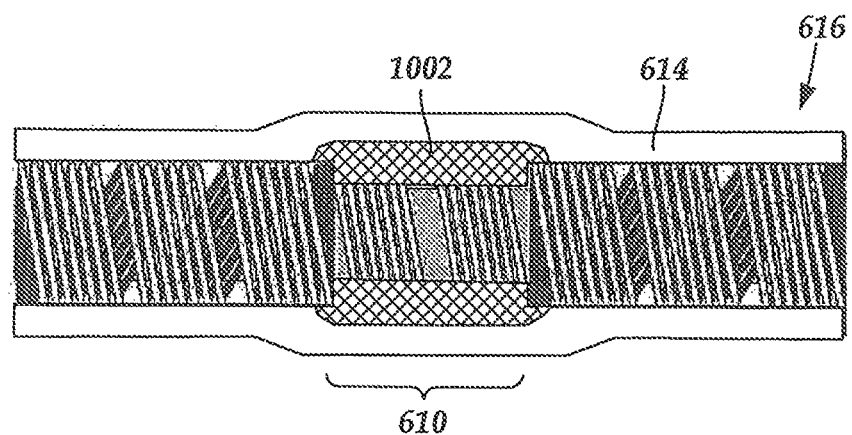
FIG. 10 is a schematic longitudinal cross-sectional view of a third embodiment of a support element disposed over the single-coil region of FIG. 6B, according to the invention.

In some embodiments, the support element includes a flowable material disposed over the single-coil region. FIG. 10 is a schematic longitudinal cross-sectional view of one embodiment of the single-coil region 610 disposed in the outer layer 614 of the lead 616. A support element 1002 includes a material disposed over the single-coil region 610 that is flowable when applied over the single-coil region 610. In at least some embodiments, the flowable material may fill in open spaces (e.g., open space 618 in FIG. 6B) formed along the length of the lead 616. In at least some embodiments, the flowable material sets or cross-links after application or flowing. In preferred embodiments, the support element 1002 is applied such that the lead 616 remains isodiametric along the portion of the lead 616 where the flowable-material support element 1002 is disposed. In other embodiments and as shown in FIG. 10, the support element 1002 may be applied such that the outer layer 614 bulges. In some embodiments, the support element 1002 may flow over time, such that bulging regions eventually distribute so that the lead 616 remains isodiametric.

Figure 11:
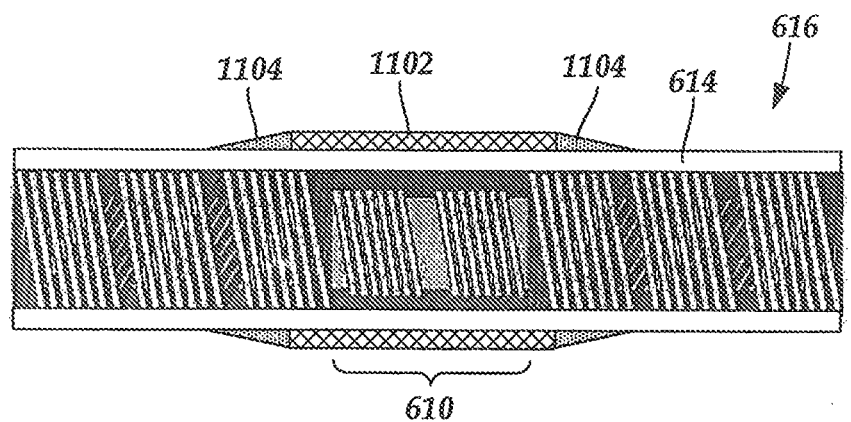
FIG. 11 is a schematic longitudinal cross-sectional view of one embodiment of a support element disposed over an outer layer of an elongated member at a location corresponding to the single-coil region of FIG. 6B, according to the invention.

In some embodiments, the support element is disposed over the outer layer of the lead. FIG. 11 is a schematic longitudinal cross-sectional view of one embodiment of the single-coil region 610 disposed in the outer layer 614 of the lead 616. A support element 1102 is disposed over the lead 616 along a portion of the lead 616 positioned over the single-coil region 610.

When the support element 1102 is disposed over the lead 616, there is a difference in diameter between an outer surface of the support element 1102 and an outer surface of the lead 616. It may be an advantage for the outer surface of the lead 616 to not have abrupt changes in diameter because abrupt changes in diameter may form ledges for an insertion needle to become caught on during insertion of the lead 616 into a patient or patient tissue during patient movement subsequent to implantation. In at least some embodiments, the support element 1102 includes tapered ends 1104 to smooth the transition in diameter from the outer surface of the lead 616 to the outer surface of the support element 1102. In at least some embodiments, separate tapering members 1104 are positioned at the ends of the support element 1102 to smooth the transition in diameter from the outer surface of the lead 616 to the outer surface of the support element 1102.

Figure 12:
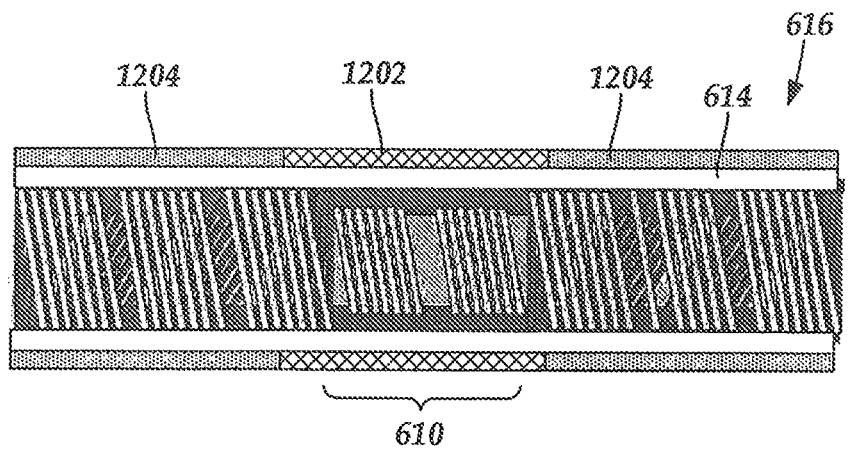
FIG. 12 is a schematic longitudinal cross-sectional view of another embodiment of a support element disposed over an outer layer of an elongated member at a location corresponding to the single-coil region of FIG. 6B, according to the invention.

In at least some embodiments, one or more additional layers are disposed over the outer layer between two or more support elements to maintain an isodiametric lead. FIG. 12 is a schematic longitudinal cross-sectional view of one embodiment of the single-coil region 610 disposed in the outer layer 614 of the lead 616. A support element 1202 is disposed over the lead 616 along a portion of the lead 616 positioned over the single-coil region 610. In at least some embodiments, one or more additional layers 1204 may be disposed over the outer layer 614 between two or more adjacent support elements 1202 to maintain an isodiametric lead. In at least some embodiments, the outer layer 614 is thicker in regions between two or more adjacent support elements 1202 to maintain an isodiametric lead.

In at least some embodiments, the support elements 702, 802, 902, 1002, 1102, and 1202 are substantially tubular. In at least some other embodiments, the support elements 702, 802, 902, 1002, 1102, and 1202 include non-tubular material (e.g., strips, sheets, coils, or the like) arranged into a tubular shape. In at least some embodiments, the support elements 702, 802, 902, 1002, 1102, and 1202 are isodiametric, thereby promoting an isodiametric lead. In at least some embodiments, the support elements 702, 802, 902, 1002, 1102, and 1202 have transverse cross-sectional shapes that form a continuous path. In at least some embodiments, the support elements 702, 802, 902, 1002, 1102, and 1202 have transverse cross-sectional shapes that form a non-continuous path.

In at least some embodiments, the support element 702, 802, 902, 1002, 1102, and 1202 is rigid. In at least some embodiments, the support element 702, 802, 902, 1002, 1102, and 1202 is flexible or bendable. In at least some embodiments, one or more characteristics of the support element 702, 802, 902, 1002, 1102, and 1202 is changed by application of a modifier. For example, heat may be added to the support element 702, 802, 902, 1002, 1102, and 1202 to heat shrink the support element 702, 802, 902, 1002, 1102, and 1202 to the single-coil region 610. In at least some other embodiments, one or more characteristics of the support element 702, 802, 902, 1002, 1102, and 1202 may be changed by application of other modifiers (e.g., an acid, a base, reduced temperature, reduced or increased pressure, and the like or combinations thereof).

In at least some embodiments, the support element 702, 802, 902, 1002, 1102, and 1202 may include one or more fluidtight reservoirs that may be filled with one or more fluids including, for example, one or more body fluids, silicone oil, water, or the like or combinations thereof. In at least some embodiments, the strength (or stiffness) of the support element 702, 802, 902, 1002, 1102, and 1202 may be adjusted by adjusting the viscosity of the fluids contained in the one or more reservoirs.

In at least some embodiments, the support element 702, 802, 902, 1002, 1102, and 1202 includes one or more accordion-like regions which may act as a shock absorber to relieve strain during bending of the conductors 602.

In at least some embodiments, the support elements 702, 802, 902, 1002, 1102, and 1202 have a longitudinal length that is greater than the diameter of the support elements 702, 802, 902, 1002, 1102, and 1202. In at least some embodiments, the support elements 702, 802, 902, 1002, 1102, and 1202 have a longitudinal length that is less than the diameter of the support elements 702, 802, 902, 1002, 1102, and 1202.

In at least some embodiments, the support elements 702, 802, 902, 1002, 1102, and 1202 are coupled to one or more of the conductor placement sleeve 612, the conductors 602, or the outer layer 614 by one or more of an adhesive, an interference fit, or the like. It will be understood that the support elements 702, 802, 902, 1002, 1102, and 1202 may be applied to the conductors either before or after the conductors are inserted into the outer layer and before or after insertion of the conductors into the outer layer 614 of the lead 616.

It will be understood that a plurality of support elements 702, 802, 902, 1002, 1102, and 1202 may be used concurrently to strengthen (or stiffen) a given single-coil region. It will also be understood that an lead 616 may include one or more different types of support elements 702, 802, 902, 1002, 1102, and 1202 positioned along different single-coil regions spaced along the longitudinal length of the lead 616.

Figure 13:
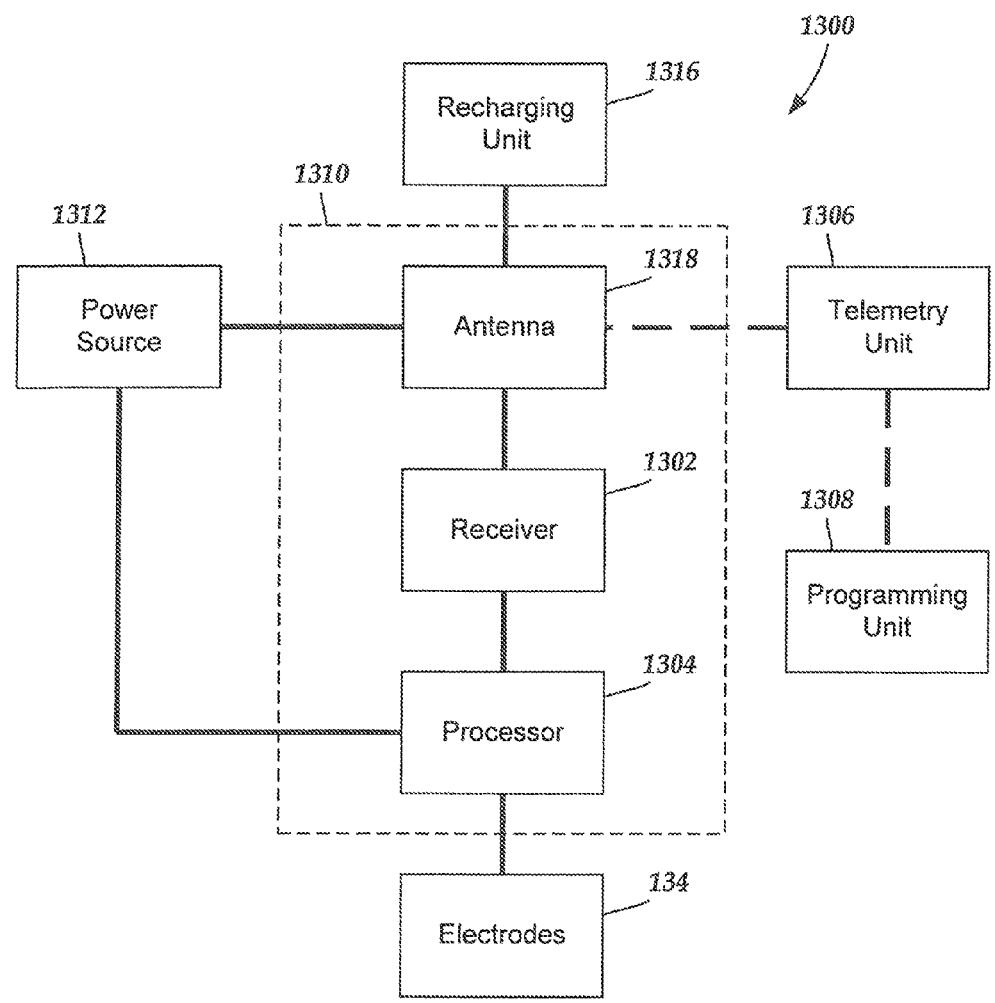
FIG. 13 is a schematic overview of one embodiment of components of a stimulation system, including an electronic subassembly disposed within a control module, according to the invention.

FIG. 13 is a schematic overview of one embodiment of components of an electrical stimulation system 1300 including an electronic subassembly 1310 disposed within a control module. It will be understood that the electrical stimulation system can include more, fewer, or different components and can have a variety of different configurations including those configurations disclosed in the stimulator references cited herein.

Some of the components (for example, power source 1312, antenna 1318, receiver 1302, and processor 1304) of the electrical stimulation system can be positioned on one or more circuit boards or similar carriers within a sealed housing of an implantable pulse generator, if desired. Any power source 1312 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Pat. No. 7,437,193, incorporated herein by reference.

As another alternative, power can be supplied by an external power source through inductive coupling via the optional antenna 1318 or a secondary antenna. The external power source can be in a device that is mounted on the skin of the user or in a unit that is provided near the user on a permanent or periodic basis.

If the power source 1312 is a rechargeable battery, the battery may be recharged using the optional antenna 1318, if desired. Power can be provided to the battery for recharging by inductively coupling the battery through the antenna to a recharging unit 1316 external to the user. Examples of such arrangements can be found in the references identified above.

In one embodiment, electrical current is emitted by the electrodes 134 on the paddle or lead body to stimulate nerve fibers, muscle fibers, or other body tissues near the electrical stimulation system. A processor 1304 is generally included to control the timing and electrical characteristics of the electrical stimulation system. For example, the processor 1304 can, if desired, control one or more of the timing, frequency, strength, duration, and waveform of the pulses. In addition, the processor 1304 can select which electrodes can be used to provide stimulation, if desired. In some embodiments, the processor 1304 may select which electrode(s) are cathodes and which electrode(s) are anodes. In some embodiments, the processor 1304 may be used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 1308 that, for example, allows modification of pulse characteristics. In the illustrated embodiment, the processor 1304 is coupled to a receiver 1302 which, in turn, is coupled to the optional antenna 1318. This allows the processor 1304 to receive instructions from an external source to, for example, direct the pulse characteristics and the selection of electrodes, if desired.

In one embodiment, the antenna 1318 is capable of receiving signals (e.g., RF signals) from an external telemetry unit 1306 which is programmed by a programming unit 1508. The programming unit 1308 can be external to, or part of, the telemetry unit 1306. The telemetry unit 1306 can be a device that is worn on the skin of the user or can be carried by the user and can have a form similar to a pager, cellular phone, or remote control, if desired. As another alternative, the telemetry unit 1306 may not be worn or carried by the user but may only be available at a home station or at a clinician's office. The programming unit 1308 can be any unit that can provide information to the telemetry unit 1306 for transmission to the electrical stimulation system 1300. The programming unit 1308 can be part of the telemetry unit 1306 or can provide signals or information to the telemetry unit 1306 via a wireless or wired connection. One example of a suitable programming unit is a computer operated by the user or clinician to send signals to the telemetry unit 1306.

The signals sent to the processor 1304 via the antenna 1318 and receiver 1302 can be used to modify or otherwise direct the operation of the electrical stimulation system. For example, the signals may be used to modify the pulses of the electrical stimulation system such as modifying one or more of pulse duration, pulse frequency, pulse waveform, and pulse strength. The signals may also direct the electrical stimulation system 1300 to cease operation, to start operation, to start charging the battery, or to stop charging the battery. In other embodiments, the stimulation system does not include an antenna 1318 or receiver 1302 and the processor 1304 operates as programmed.

Optionally, the electrical stimulation system 1300 may include a transmitter (not shown) coupled to the processor 1304 and the antenna 1318 for transmitting signals back to the telemetry unit 1306 or another unit capable of receiving the signals. For example, the electrical stimulation system 1300 may transmit signals indicating whether the electrical stimulation system 1300 is operating properly or not or indicating when the battery needs to be charged or the level of charge remaining in the battery. The processor 1304 may also be capable of transmitting information about the pulse characteristics so that a user or clinician can determine or verify the characteristics.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. An implantable lead comprising:
    a lead body comprising an outer layer and having a distal end portion, a proximal end portion, and a longitudinal length;
    a plurality of electrodes disposed along the distal end portion of the lead body;
    a plurality of terminals disposed along the proximal end portion of the lead body;
    a plurality of conductors disposed within the outer layer of the lead body, each conductor of the plurality of conductors electrically coupling at least one of the plurality of electrodes to at least one of the plurality of terminals, wherein at least one of the plurality of conductors comprises a plurality of units, each of the units comprising
        a first conductor segment extending along the lead body from a beginning point to a first position,
        a second conductor segment extending from the first position to a second position, and
        a third conductor segment extending along the elongated member from the second position to an endpoint,
        wherein the conductor segments are arranged so as to form a plurality of single-coil regions and a plurality of multi-coil regions,
        wherein the plurality of single-coil regions and the plurality of multi-coil regions are arranged along the longitudinal length of the lead body in an axially alternating configuration with each individual single-coil region of the plurality of single-coil regions abutted by at least one multi-coil region of the plurality of multi-coil regions,
        wherein the single-coil regions have a first stiffness and the multi-coil regions have a second stiffness that is greater than the first stiffness; and
    a plurality of discontinuous, axially-spaced-apart support elements configured and arranged to increase stiffness solely along selected regions of the lead, wherein for each of the plurality of single-coil regions one of the support elements is disposed beneath the single-coil region to decrease differences in stiffness between the single-coil region and the at least one multi-coil region abutting the single-coil region.

2. The lead of claim 1, further comprising a conductor placement sleeve extending along at least a portion of the lead body, wherein at least one of the conductor segments is wrapped around the conductor placement sleeve.

3. The lead of claim 2, wherein at least one of the plurality of support elements comprises a reinforced region of the conductor placement sleeve positioned beneath at least one of the single-coil regions.

4. The lead of claim 3, wherein the at least one reinforced region of the conductor placement sleeve comprises a region of the conductor placement sleeve having an increased thickness as compared to regions of the conductor placement sleeve positioned beneath at least one of the multi-coil regions.

5. The lead of claim 3, wherein the at least one reinforced region of the conductor placement sleeve comprises a region of the conductor placement sleeve formed from a material having an increased stiffness as compared to material used to form regions of the conductor placement sleeve positioned beneath at least one of the multi-coil regions.

6. The lead of claim 2, wherein at least one of the plurality of support elements is disposed over a portion of the conductor placement sleeve.

7. The lead of claim 1, wherein the plurality of support elements increase the stiffness of the single-coil regions by at least 5%.

8. The lead of claim 1, wherein the plurality of support elements are radiopaque.

9. The lead of claim 1, wherein at least one of the plurality of support elements comprises at least one fluid-filled reservoir.

10. The lead of claim 1, wherein at least one of the plurality of support elements comprises at least one material that is flowable when applied to the conductor and configured and arranged to set or cross-link after flowing.

11. The lead of claim 1, wherein at least one of the plurality of support elements comprises a material that is at least one of braided, coiled, or formed as a mesh.

12. The lead of claim 11, wherein the material is encased in a polymer.

13. The lead of claim 1, wherein the lead is isodiametric.

14. The lead of claim 1, wherein at least one of the plurality of support elements is tubular.

15. An electrical stimulating system comprising:
the lead of claim 1;
a control module configured and arranged to electrically couple to the lead, the control module comprising
a housing, and
an electronic subassembly disposed in the housing; and
a connector having a proximal end, a distal end, and a longitudinal length, the connector configured and arranged to receive the lead, the connector comprising
a connector housing defining a port at the distal end of the connector, the port configured and arranged for receiving the proximal end portion of the lead body of the lead, and
a plurality of connector contacts disposed in the connector housing, the connector contacts configured and arranged to couple to at least one of the plurality of terminals disposed on the proximal end portion of the lead body.

16. The electrical stimulating system of claim 15, wherein the connector is disposed on the control module.

17. The electrical stimulating system of claim 15, further comprising a lead extension having a proximal end and a distal end, the connector disposed on the distal end of the lead extension.

18. The electrical stimulating system of claim 17, wherein the proximal end of the lead extension is configured and arranged for insertion into another connector.

19. A method for forming an implantable lead, the method comprising:
forming an elongated conductor into a plurality of units, the plurality of units comprising
a first conductor segment extending in a first direction from a beginning point to a first position,
a second conductor segment extending in a second direction that is opposite to the first direction from the first position to a second position, and
a third conductor segment extending in the first direction from the second position to an endpoint,
wherein the conductor segments are arranged so as to form a plurality of single-coil regions and a plurality of multi-coil regions,
wherein the plurality of single-coil regions and the plurality of multi-coil regions are arranged in an axially alternating configuration with each individual single-coil region of the plurality of single-coil regions abutted by at least one multi-coil region of the plurality of multi-coil regions,
wherein the single-coil regions have a first stiffness and the multi-coil regions have a second stiffness that is greater than the first stiffness;
disposing a plurality of discontinuous, axially-spaced apart support elements beneath the conductor to increase stiffness solely along selected regions of the conductor;
disposing the conductor in an elongated outer layer;
coupling a first end of the conductor to an electrode; and
coupling a second end of the conductor to a terminal.

20. The method of claim 19, wherein for each of the plurality of single-coil regions one of the support elements is disposed beneath the single-coil region to decrease differences in stiffness between the single-coil region and the at least one multi-coil region abutting the single-coil region.

* * * * *